United States Patent
Parisotto et al.

(10) Patent No.: US 9,962,479 B2
(45) Date of Patent: May 8, 2018

(54) METHOD TO CONTROL A BLOOD TREATMENT APPARATUS AND DEVICES AFTER THE CONCLUSION OF TREATMENT

(71) Applicant: FRESENIUS MEDICAL CARE DEUTSCHLAND GMBH, Bad Homburg (DE)

(72) Inventors: Maria Teresa Parisotto, Bad Homburg (DE); Wolfgang Wehmeyer, Tübingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 201 days.

(21) Appl. No.: 14/905,445

(22) PCT Filed: Jul. 15, 2014

(86) PCT No.: PCT/EP2014/065121
§ 371 (c)(1),
(2) Date: May 18, 2016

(87) PCT Pub. No.: WO2015/007722
PCT Pub. Date: Jan. 22, 2015

(65) Prior Publication Data
US 2016/0250406 A1    Sep. 1, 2016

(30) Foreign Application Priority Data
Jul. 15, 2013    (DE) .................... 10 2013 011 717

(51) Int. Cl.
*A61M 1/36*    (2006.01)
*A61M 1/26*    (2006.01)
(Continued)

(52) U.S. Cl.
CPC ........ *A61M 1/3643* (2013.01); *A61M 1/1601* (2014.02); *A61M 1/267* (2014.02);
(Continued)

(58) Field of Classification Search
CPC .... A61M 1/1601; A61M 1/168; A61M 1/267; A61M 1/3626; A61M 1/3643; A61M 1/3644; A61M 1/3646; A61M 1/365; A61M 1/3652; A61M 1/3653; A61M 2202/0413; A61M 2205/3331; A61M 2205/52; A61M 39/28
See application file for complete search history.

(56) References Cited

FOREIGN PATENT DOCUMENTS

| DE | 34 42 744 A1 | 6/1986 |
|---|---|---|
| DE | 10323843 | 12/2004 |

(Continued)

OTHER PUBLICATIONS

International Search Report from PCT/EP2014/065121, dated Feb. 5, 2015.

*Primary Examiner* — John Kim
(74) *Attorney, Agent, or Firm* — Fish & Richardson P.C.

(57) ABSTRACT

The present invention relates to a method for controlling a blood treatment apparatus to automatically move it into a certain state after completion of the treatment of a patient carried out with the blood treatment apparatus. It also relates to a control and regulating device and a treatment apparatus. It further relates to a computer program, a computer program product as well as a digital storage medium.

7 Claims, 2 Drawing Sheets

(51) Int. Cl.
*A61M 1/16* (2006.01)
*A61M 39/28* (2006.01)
(52) U.S. Cl.
CPC .......... *A61M 1/365* (2014.02); *A61M 1/3644* (2014.02); *A61M 1/3652* (2014.02); *A61M 1/3653* (2013.01); *A61M 39/28* (2013.01); *A61M 1/168* (2013.01); *A61M 1/3626* (2013.01); *A61M 1/3646* (2014.02); *A61M 2202/0413* (2013.01); *A61M 2205/3331* (2013.01); *A61M 2205/52* (2013.01)

(56) References Cited

FOREIGN PATENT DOCUMENTS

| DE | 602 24 687 T2 | 1/2009 |
|----|---------------|--------|
| EP | 2 564 884 A1  | 3/2013 |
| WO | 9625214       | 8/1996 |
| WO | 2011063923 A1 | 6/2011 |
| WO | 2013024825 A1 | 2/2013 |

METHOD TO CONTROL A BLOOD TREATMENT APPARATUS AND DEVICES AFTER THE CONCLUSION OF TREATMENT

CROSS REFERENCE TO RELATED APPLICATIONS

The present application is the national stage entry of International Patent Application No. PCT/EP2014/065121, filed on Jul. 15, 2014, the disclosure of which is expressly incorporated herein in its entirety by reference thereto, and claims priority to Application No. DE 10 2013 011 717.8, filed in the Federal Republic of Germany on Jul. 15, 2013.

FIELD OF INVENTION

The present invention relates to a method to control or for controlling a blood treatment apparatus, in particular at the conclusion of a blood treatment of a patient. It further comprises a control or regulating device, a blood treatment apparatus, a computer programme, a computer programme product and a digital storage medium.

BACKGROUND

Methods to control a blood treatment apparatus are known from practice, inter alia for bringing those as well as further devices into a specific condition by means of rinsing and cleaning etc., which is carried out on the blood treatment apparatus and the further devices after the conclusion of the treatment of a patient.

SUMMARY

One object of the present invention is to propose a further method for controlling or to control a blood treatment apparatus. Additionally, a control or regulating device and a blood treatment apparatus are proposed. Furthermore a computer programme, a computer programme product and a digital storage device shall be proposed.

The object of the present invention can be solved or achieved through a method of the present invention. It can additionally be achieved by means of a control or regulating device, a blood treatment apparatus, a computer programme, a computer programme product and a digital storage device.

Thus, according to the present invention an automatic method is proposed for controlling a blood treatment apparatus, in particular after a blood treatment carried out by means of the blood treatment apparatus. The blood treatment apparatus contains a blood pump for conveying blood situated in an extra-corporeal blood circuit. The blood tube set comprises an arterial section which contains or is connected to, an arterial needle, and which has a arterial patient tube clamp. The blood tube set additionally comprises a venous section which contains or is connected to a venous needle and which has a venous patient tube clamp. Between the arterial and venous section at least one blood filter is arranged. This comprises a membrane. The membrane separates a blood chamber from a dialysis fluid chamber.

The method according to the present invention comprises some or all of the following steps in any combination:
a) closing the arterial patient tube clamp and the venous patient tube clamp;
b) delivery of dialysis fluid by means of the dialysis fluid pump;
c) opening of the venous patient tube clamp.
d) closing the dialysate drain tube.
e) stopping the flow of dialysis fluid, in particular as soon as a pre-determined first volume less a second volume crosses over or passes through the membrane or is delivered by means of the dialysis pump, in which for example the first volume consists of the total volume, contained in the extra-corporeal blood circuit on the blood side (about its capacity or its priming volume), and in which for example the second volume is likewise pre-determined or for example can correspond to the volume of the arterial section of the extra-corporeal blood circuit to the inlet of the blood filter or to additionally include the capacity of the blood chamber of the blood filter; the pre-determined first volume less the second volume in certain embodiments according to the present invention equates to the priming volume or capacity of the arterial sections of the extra-corporeal blood circuit used (alternatively with or without the capacity of the blood chamber of the blood filter);
f) closing of the venous patient tube clamp;
g) conveying of dialysis fluid by means of the dialysis fluid pump;
h) opening the arterial patient tube clamp by closed dialysis drain tube.
i) optionally: reducing of the conveying rate by means of the dialysis fluid pump;
j) closing of the arterial patient tube clamp;
k) stopping the dialysis fluid when the second volume is achieved or when by means of a sensor, in particular by means of an air bubble detector upstream of the arterial patient tube clamp, air or clots are detected, or immediately another pre-determined criterion is fulfilled (for example the result of a sensor measurement); the second volume can correspond to the arterial rinse-back volume.

The method according to the present invention further comprises, optionally, the steps 1) to q) or alternatively steps r) to s), or any combination or sub-combination hereof in any combination:
l) starting a dialysis fluid pump lying or located downstream of a blood filter, or a dialysis pump) lying or located upstream of a blood filter in particular in reverse;
m) closing, holding closed or opening the dialysis fluid supply tube;
n) opening, holding open or closing the dialysis drain tube clamp;
o) closing or holding closed the arterial and venous patient tube clamps;
p) opening a vent valve combined or provided with the venous blood chamber, in for example a connecting tube with venous pressure sensor or between a venous pressure transducer and a venous pressure sensor;
q) sucking or aspirating dialysis fluid over or through the membrane out from the blood tube set by means of the dialysis fluid pump.
r) opening the dialysate drain tube so that flow through its lumen or discarding of fluid over the dialysate drain tube, for example via the drain, is possible;
s) introducing gas, for example air in the connecting tube for example between a venous pressure transducer and a venous pressure sensor. The gas can for example be introduced by means of a compressor. The gas displaces the dialysate over or through the membrane on the dialysate outlet side where it will be led away into the drain;

The method according to the present invention further comprises, optionally, at least one or more of the following steps;

t) optionally: emptying the container with dry bicarbonate concentrate, for example, via the drain, for example for discarding the remaining bag contents;

u) stopping the dialysis fluid pump;

v) closing of the arterial patient tube clamp, venous patient tube clamp, and if applicable also the substituate clamp (or infusate clamp) for sealing a tube for supplying substitute if not yet done; and w) Optionally: outputting, in particular for the first time since the start of the method according to the present invention, alarms or indicators to inform dialysis personnel of the end of the process.

The steps t) to w) can start or fully complete before, parallel to, or after the steps 1) to s) (where provided) or at their beginning.

The sequences, in particular of steps t) to w) can be as described here. The steps can also run in other or any sequence, where provided. The same applies in some embodiments according to the present invention for all steps according to the present invention. They can also run in any other order as herein described, where seen to be technically possible by someone skilled in the art and will also fall under the present invention.

Between steps f) and g) a further step can be executed which serves to create or to ensure a continuous pump tube section. This passage can for example, be achieved, as indicated below by the pump tube section being brought out of engagement with the pump, which is most often an occluding pump. To this end the pump tube section, hence the tube section in contact with the moving body of the pump can be ejected. The latter can be achieved for example by opening, loosening or ejecting the so called Alpha-Clips explained further below. This method step is referred to below as step f1). An integrated pump tube section can also be achieved or ensured by method step identified here as f2) in which a pump in engagement with a pump tube section is rotated against its usual direction, that is in reverse, particularly synchronous to the dialysis fluid pump.

The optional reduction of conveying rate of the dialysis fluid pump according to method step i) can mean a reduction of the conveying rate of 20%, 30%, 40%, 50%, 60%, 70% or 80% of the normal or average conveying rate during the treatment, preferably a halving.

The term "downstream" or "downstream of" herein refers to the (blood or dialysis fluid—) direction of flow during the treatment of the patients. The arterial section of the blood tube set thus lies upstream of the blood filter. The venous section of the blood tube set therefore lies downstream of the blood filter.

The control or regulating device according to the present invention is set up, configured, specified and/or programmed such that it performs or causes to perform the method according the present invention in interaction with one blood treatment apparatus arranged with one of the hereto required devices.

The blood treatment apparatus according to the present invention comprises a control or regulating device according to the present invention or is connected hereto.

The computer programme according to the present invention can be loaded directly into the internal memory of a digital computer and comprises software code sections with which the steps of the method according to the present invention are or can be executed when the computer programme runs on a computer.

The digital storage medium according to the present invention comprises electronically readable control signals, which can interact with a programmable computer system or computer such that the steps of the method according to the present invention are caused to happen or prompted.

An especially digital, in particular non-volatile (here also referred to as carrier), storage medium according to the present invention, particularly in the form of disk, RAM, ROM, CD, hard drive, DVD, USB stick, flash card, SD card or EPROM, especially with optically or electronically readable control signals, can interact with a programmable computer or a computer system, in such a way that the automated steps of a method according to the present invention described herein are initiated.

Thereby all, many or some of the machine-implemented steps of the method according to the present invention can be initiated.

A computer programme product according to the present invention comprises a programme code stored on a machine readable carrier or storage medium for prompting the steps of the method according to the present invention, when the computer programme product runs on a computer. A computer programme product according to the present invention is understood for example to be a carrier stored programme, an embedded system as a comprehensive system with a computer programme (such as an electronic device with a computer program), a network of computer implemented computer programmes (such as client/server system, cloud computing system, etc.) or a computer on which a computer programme is loaded, runs, is saved, executed or developed or designed.

A machine-readable carrier comprises in certain embodiments according to the present invention a carrier containing data and/or information interpretable by software and/or hardware. The carrier can be a floppy disk, CD, DVD, USB stick, flash card, an SD card, and the like.

A computer programme according to the present invention comprises a programme code for prompting the mechanical steps of the method according to the present invention when the computer programme runs on a computer. A computer programme according to the present invention can be understood for example, as a physically, marketable software product distribution which comprises a program.

Applicable to the computer programme product according to the present invention and also to the computer programme according to the present invention is that all, many or some of the machine initiated steps of the method according to the present invention are prompted or brought about.

For all previous and following disclosure or explanations it is to be understood that the use of the terms "can be" and "can have" etc. are synonymous with "is preferably" and "has preferably" etc. and shall explain an embodiment according to the present invention.

Embodiments according to the present invention can comprise one or more of the features mentioned below.

The venous patient tube clamp is in some embodiments according to the present invention any type of device to interrupt the flow in the venous section of the blood tube set downstream of the blood filter.

The arterial patient tube clamp is in some embodiments according to the present invention any type of device to interrupt the flow in the arterial section of the blood tube set downstream of the blood filter.

In certain embodiments according to the present invention, the method comprises stopping the blood pump to conclude a previously running blood treatment according to the present method, when one of the following conditions is met:

reaching a given point in time (e.g. a time of day);

reaching a pre-determined or pre-defined duration of treatment, for example the effective dialysis time (that is the period of time, during which the dialysis fluid flow is flowing through the dialyzer or blood filter, or during which the blood filtrate is withdrawn; in some embodiments according to the present invention, times during which just for ultra-filtration takes place do not count towards the effective dialysis time);

reaching a pre-determined dialysis dosage value (for example, the ratio Kt/V (after Gotch and Sargent, for example, with K as a measure of the clearance, t as the length of the effective dialysis time in minutes, and V as an indication of 60% of the body mass (weight), in which the blood can circulate (body water content); or reaching a pre-defined or pre-determined ultra-filtration quantity.

In some of these embodiments according to the present invention, no alarm or any communication due to the stoppage of the blood pump is given, since the involvement of the staff is not required until further notice. In certain of these embodiments according to the present invention, the method comprises monitoring whether any of the above criteria are satisfied or met. Appropriate sensors, timers or other devices are provided.

In certain embodiments according to the present invention, neither an alarm nor a notification is given to the staff between each all or some of the successive steps. The blood treatment apparatus in these embodiments according to the present invention, takes the respective steps and transitions in the pre-defined or pre-determined order spontaneously or independently or automatically. There is no need in these embodiments according to the present invention for the involvement of staff. Information to the staff configured in any manner (visual, acoustic, etc., and combinations thereof) about the status of the method in these embodiments according to the present invention is therefore unnecessary and can be omitted, although such information may optionally be provided.

In some embodiments according to the present invention the method comprises an automatic ejection of or automatically ejecting the blood tube section in the blood tube set by means of a device, for example using the so-called ALPHA clip, which is disclosed by the assignee of the present invention for example in International Patent Publication No. WO 2005/111424 A1 as an adapter 32 or fitting 14. The corresponding disclosure of that document is hereby fully incorporated by reference.

In some embodiments of the method according to the present invention the dialysis fluid flow rate is automatically adjusted in step b). The change may be a reduction of a previously set dialysis fluid rate, it can be an increasing, a decreasing or another change, for example, one that leads to a pulsation of the dialysis fluid flow. This can advantageously assist or effect a release of cell or protein elements in the filter.

In some embodiments according to the present invention, the method comprises one or more of the following, either automatically or manually performed steps:

separating the dialysate connectors (connecting sections by which the blood filter on the side of its dialysis fluid chamber is removably connected to the hydraulics of the blood treatment apparatus) and/or an online connector, or similarly preventing a fluid communication with the hydraulics by means of valves; in this way a switching of the blood tube set into a bypass position is accomplished, i.e. the dialysate connectors (now fluid free, since sucked empty) as well as the online connector are separated from the hydraulics by means of valves;

disconnecting the dry bicarbonate concentrate container from the hydraulics or preventing a fluid communication between the container and hydraulics;

the disinfection takes place until detected on the machine side so that the purging of the not connected hydraulic part is necessary and the blood treatment apparatus goes into the so called HOLD status.

In some embodiments according to the present invention the method comprises an automatically initiated blood pressure measurement. The results can be forwarded. An evaluation of the same is not part of the present method.

In some embodiments according to the present invention, the method comprises a check as to whether the dialysate drain tube and the dialysis fluid supply tube have been connected to the machine, if the online connector is in the purge position and/or whether the container with the dry bicarbonate concentrate has been removed. If one or all of these tests, for example all three tests are positive, then in some embodiments according to the present invention the disinfection is continued.

In certain embodiments according to the present invention, the method comprises adding back or calculating the pre-determined amount of the first volume to the ultra-filtration amount, in particular before the start of the blood treatment.

In some embodiments according to the present invention, the blood treatment apparatus is configured for dialysis, acute dialysis, chronic dialysis, and chronic hemodialysis, in particular for double needle dialysis.

In certain embodiments according to the present invention, the method comprises the steps in the sequence specified herein or in the alphabetical order described.

In some embodiments according to the present invention each step is automatically initiated and carried out In certain embodiments of the method according to the present invention, some (any) or all of the individual steps are prompted or executed without any intermediate steps after the previous or prior step.

In some embodiments according to the present invention it is provided that the forthcoming step will not start before the respective preceding step has ended. In certain embodiments according to the present invention it is provided that between some or all of the respective directly successive steps of the method according to the present invention here for example designated as prior and subsequent steps a minimum time (the minimum period may be a time delay of pre-determined duration in which the system does not respond or can proceed) after the end of the prior step is waited, before the successive step can be initiated. An example of the prior step is particularly step e). The passing of the minimum time, where provided, can be ensured according to the present invention by any suitable blocking of the system, such as a temporary de-energizing of the corresponding system, or similar device. The control or regulating device according to the present invention can be programmed accordingly. In this way, it may be advantageously possible to avoid undesired pressure conditions, which arise, for example by a pump starting when a clamp is still closed and can lead to endangering patient safety through the possibility of bursting tubes, or for example can lead to adverse effects on the blood exposed to the raised pressure. Thus it can be provided that the moving components of a (any) pump must be reliably brought to a standstill or stop before the subsequent step can be begun. Exemplarily it can be provided that a clamp opens or closes only when a pump in fluid communication with same clamp is completely and bindingly stopped. For this purpose waiting a minimum time can contribute beneficially or advantageously.

The minimum time can have a value between 0.5 sec and 20 sec (seconds) preferably between 1 and 10 sec, more preferably between 2 and 5 sec.

The minimum time may be fixed, but it may also be variable, for example dependent on sensor results, etc.

In some embodiments according to the present invention, the blood circuit or the blood tubing system is not short-circuited during the execution of the method according to the present invention, in particular not by means of a connector, which exemplarily connects the venous section to the arterial section.

Each of the devices of the apparatus according to the present invention referred to herein, may be specifically adapted, configured and/or programmed, controlled or otherwise prepared to carry out the respective method step, even if this is not explained specifically herein.

For each method step described herein, some of the devices according to the present invention comprise each of the devices required for its execution.

The findings and definitions applicable to the device according to the present invention apply always, where this leads to no inconsistency or contradiction for one skilled in the art, also to the method according to the present invention and vice versa.

Some or all embodiments according to the present invention can comprise one, more or all of the advantages mentioned above or in the following.

By this means the time taken by the dialysis personnel for the dismantling, flushing etc of the utilised blood treatment apparatus can advantageously be reduced. Improved time management and a potential for the saving of staff time can result from this. Furthermore or additionally, errors, which can always accompany the manual execution of operations, may be avoided for example that working steps can not be forgotten or performed in reversed order.

In some embodiments according to the present invention, one can advantageously waive or dispense with short-circuiting certain parts of the blood treatment apparatus, in particular short-circuiting a venous section with an arterial section, for example of the blood tubing system and/or of the blood circuit.

Furthermore, the present invention allows hygiene to be improved, as repeated connection of formerly sterile components is not necessary, such as when/by connecting the arterial section of the so-called safe-line.

Furthermore, the present invention allows an improved human-machine interaction. For example, the accuracy of the operation of the apparatus according to the present invention is improved, for example by adherence to minimum times, see above.

Finally, the mental effort of the operator is advantageously reduced by carrying out the method according to the present invention The present invention is exemplarily explained in the following with reference to the accompanying drawing, in which identical reference numerals denote identical or similar components. In the partly highly simplified drawings

DETAILED DESCRIPTION

Figure 1:
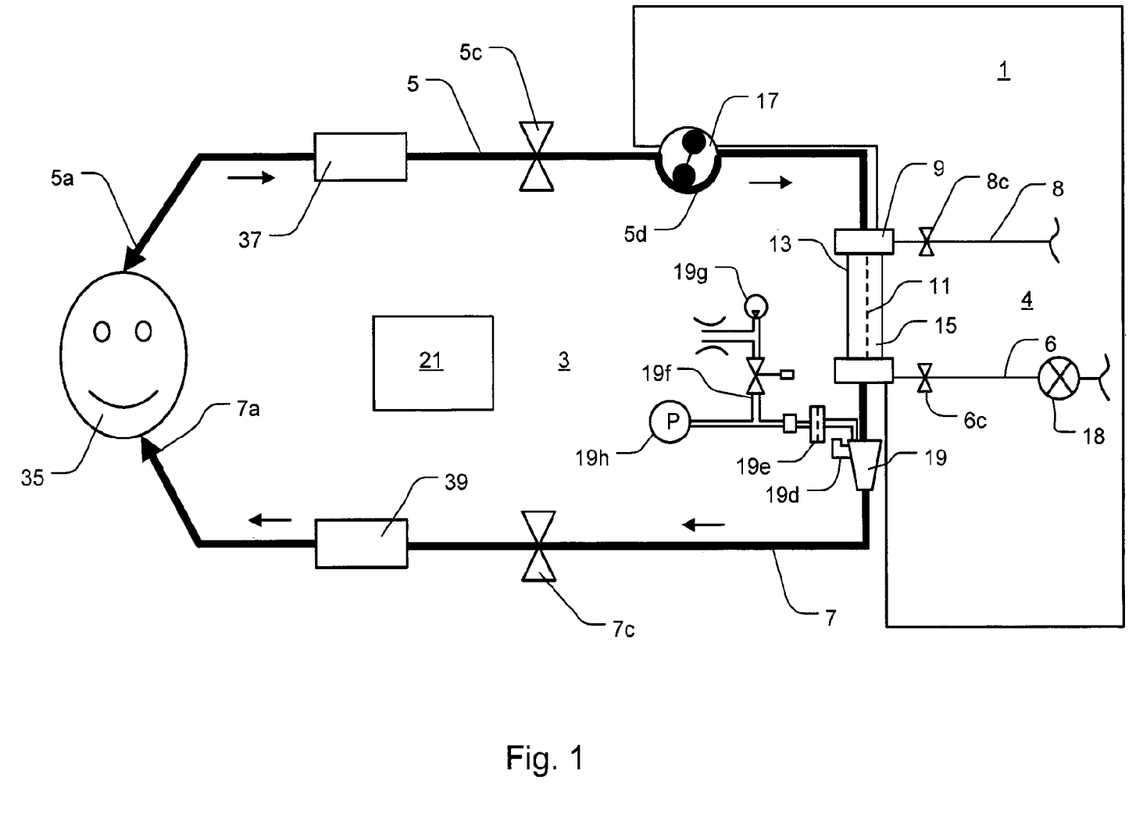
FIG. 1 shows schematically simplified an apparatus according to the present invention to perform the method according to the present invention.

FIG. 1 shows schematically simplified of a blood treatment apparatus 1 according to the present invention which is connected to a blood tube set 3. The blood tube set 3 has an arterial section 5 with an arterial needle 5a and an arterial patient tube clamp 5c. The blood tube set 3 further comprises a venous section 7 with a venous needle 7a and a venous patient tube clamp 7c.

The blood tube set 3 has or comprises a blood filter 9 with a membrane 11, for example a semi-permeable membrane. The membrane 11 divides the blood filter 9 into a blood chamber 13 and a dialysis fluid chamber 15.

The blood treatment apparatus 1 comprises or has a blood pump 17. The blood tube set has or comprises a venous drip chamber 19. The blood treatment apparatus 1 has a control or regulating device 21 or is connected to it. The control or regulating device 21 is connected to all components of the blood treatment apparatus 1 or of the blood tube set 3, or both, on which it must act to perform the method according to the present invention.

Both the arterial needle 5a and the venous needle 7a are connected to the vascular system of a patient 35. The blood tube set 3 comprises optionally an arterial air bubble detector 37 or a venous blood sensor 39 or both.

The blood treatment apparatus 1 further comprises a conveying device with at least one dialysis fluid pump 18 for conveying dialysis fluid within a closed or open dialysis fluid circuit 4. The dialysis fluid circuit 4 has a dialysis fluid supply tube 6 which can be closed by means of a dialysis fluid supply tube clamp 6c of the blood treatment apparatus 1 and a dialysate drain tube 8 which can be closed by means of a dialysate drain tube clamp 8c of the blood treatment apparatus 1. The control or regulation device 21 is connected to all components of the conveying device or the dialysis fluid circuit 4, or both, with which it must interact to carry out the method according to the present invention.

The arterial section 5 of the blood tube set 3 has or comprises a blood tube section 5d.

The venous drip chamber 19 has a venting valve 19d.

Additionally, the venous drip chamber 19 is connected with a tube or connecting tube, which is connected to a compressor 19g via an optionally provided sterile filter 19e and an optional present valve 19f. Additionally, this same tube is connected to a venous pressure sensor 19h in the exemplary embodiment shown here.

The elements 19e to 19h are shown for illustration purposes within the blood tube set 3. They can also, however, separately or together be part of the blood treatment apparatus 1. This is especially true for the compressor 19g, the valve 19f and pressure sensor 19h.

Figure 2:
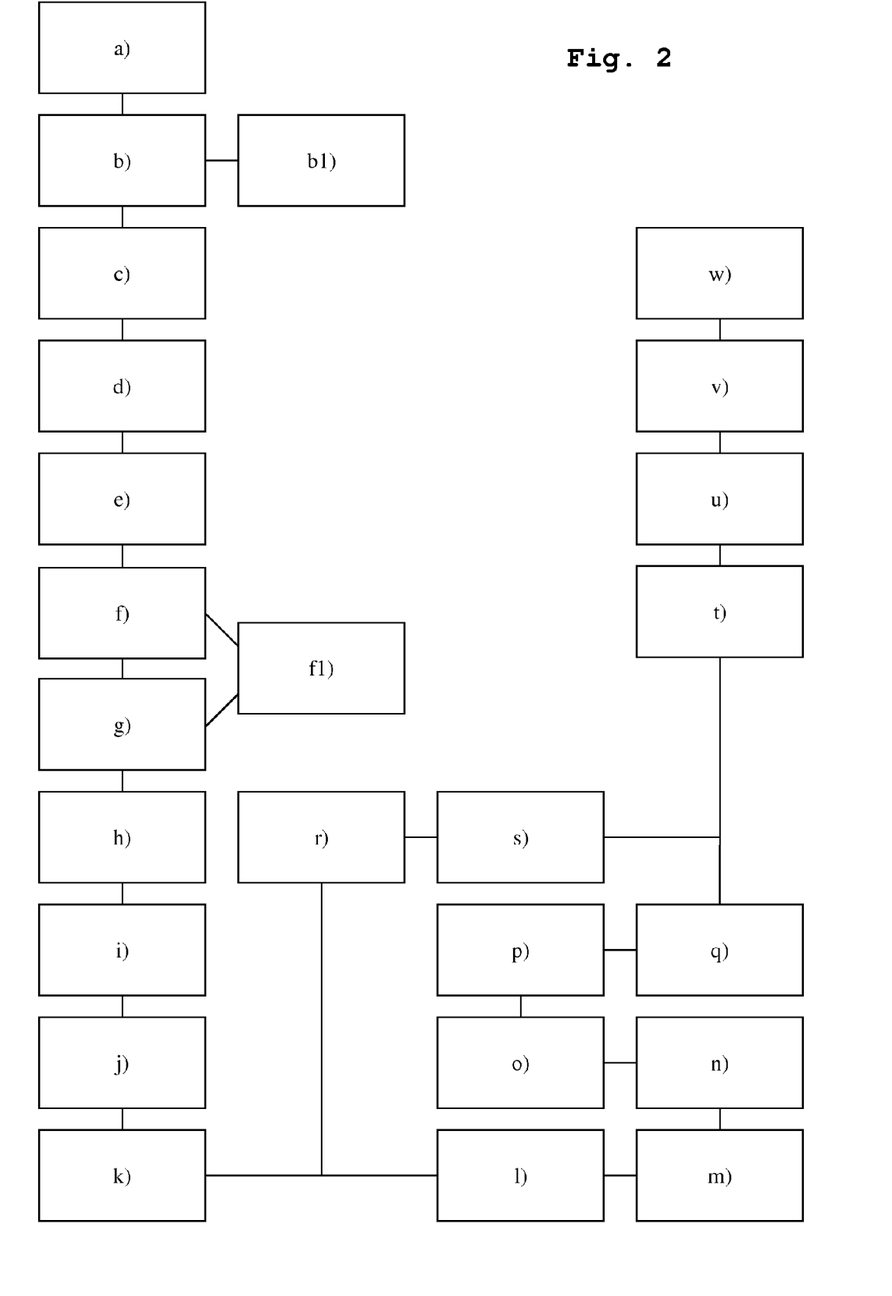
FIG. 2 shows schematically in a flow diagram, the steps of the method according to the present invention in a first exemplary embodiment.

FIG. 2 shows schematically simplified a flow diagram of the sequence of the method according to the present invention in a first exemplary embodiment.

The method begins in this embodiment, in step a) with the closing of the arterial patient tube clamp 5c and of the venous patient tube clamp 7c.

In step b) the flow of dialysis fluid delivered by means of the dialysis fluid pump 18 is reduced or adjusted automatically to a pre-determined value.

The pre-determined value can correspond to that of the known rinse back process (e.g. 100 ml/min). Step b) can in particular directly follow step a).

The optional step b1) provides for the dialysis fluid flow being constant or not constant in step b). The latter can for example be effected by means of a pulsating variation, with the aim of freeing cell and protein elements deposited in the fibre volume of the blood filter 9.

In step c) the venous patient tube clamp 7c is opened, which has been closed in step a) to obtain a so-called safe condition of the blood treatment apparatus at the close of the blood treatment.

In step d) the dialysate outlet of the blood filter 9 is closed. This can be done by, for example, closing a dialysate supply tube 8 with dialysate supply tube clamp 8c. Thus dialysis fluid enters the lumen of the blood filter 9 through the membrane 11 out of or from the dialysis fluid circuit 4 and finally from there through the venous section 7 into vascular system of the patient 35.

Step e) provides for stopping, interrupting or inhibiting flow of dialysis fluid reached or conveyed or delivered by the dialysis fluid pump 18. This can be done by controlling or altering or stopping the dialysis fluid pump 18. Alternatively or additionally, this can also be done by altering or closing the flow path of the dialysis fluid.

The stopping interrupting or inhibiting in certain embodiments according to the present invention is achieved in particular when (if) a first volume less a second volume has passed over or through the membrane 11. The first volume may correspond to a pre-determined value which would be set for example by the staff of the dialysis treatment apparatus. Its value may be defined as above. Its size can be determined automatically by the treatment apparatus and/or taken from lists. The second volume, also referred to as a delta, corresponds to the volume of the entire arterial section 5 of the extracorporeal blood circuit 3 as far as the inlet of the blood filter 9.

Before, with or after step e) the venous patient tube clamp 7c is closed in a step f).

In turn, in optional step f1)—as part of an alternative possibility—a blood tube section 5d of the blood tube set 3 inserted into the blood pump 17, is ejected by a suitable device, for example, the so-called ALPHA-clip, or released automatically from the blood pump 17 by other means.

In the subsequent step g) dialysis fluid is conveyed by means of the dialysis fluid pump 18 with previously, simultaneously or subsequently opened arterial patient tube clamp 5c (step h), and further closed dialysate drain, such as closed dialysate drain tube 8.

In optional step i), the conveying rate of the dialysis liquid pump 18 is reduced. It thus advantageously releases as few clots as possible. The reduced conveying rate may in turn be for example, 50% of the treatment conveying rate, see above.

In step j), the arterial patient tube clamp 5c is closed.

In step k) the dialysis fluid 18 is stopped or—alternatively or additionally—another measure to prohibit the dialysis fluid flow is taken as soon as the second pre-determined volume has been delivered by means of dialysis fluid pump 18. The second pre-determined volume may be the arterial rinse back volume. Alternatively the detection of air bubbles or blood clots by means of the corresponding sensors is promoted.

The method further comprises, optionally, the following steps, or alternatively the steps l) to q), or the steps r) and s):

In step l), for example situated downstream of the blood filter 9, a not shown, ultra filtration pump or an also not shown dialysis fluid pump (or, more correctly dialysate pump) is started. The dialysis fluid supply tube 6 is kept or held closed (step m)). The dialysis fluid tube clamp 8c is opened. The arterial and venous patient tube clamps 5c, 7c are kept or held closed (step o)).

In some embodiments according to the present invention, for step l) the ultra-filtration pump (not shown in the figures) is set in operation to empty according to step l. Again, alternatively, in certain embodiments of the present invention for step l) the compressor 19g (see FIG. 1) is put into operation. Finally, a combined use of (any) two or three of the aforementioned pumps may be used for emptying the lumen in step l).

In step p) a vent valve 19d is opened. By way of example, the vent valve can be provided in the venous drip chamber 19 or in a connecting line to the venous drip chamber 19 which comprises a venous pressure transducer and/or a venous pressure sensor 19h.

In step q), by means of the dialysis fluid pump 18, the dialysis fluid is sucked over the membrane 11 out of the blood tube set 3.

In optional step t) the container of dry bicarbonate concentrate (not illustrated) is emptied.

In the alternative or complementary steps r) to s) the dialysate drain tube 8 is opened (step r)).

In step s) gas, such as air, is introduced into the connecting tube comprising the venous pressure sensor 19h, or in another position, for example by means of the compressor 19g. The gas displaces the dialysate through the membrane 11 into the dialysis fluid chamber 15. From there it passes through the dialysate drain tube and an opened valve into the drain.

With step t) the container with dry bicarbonate concentrate is emptied

Afterwards the method comprises stopping the dialysis fluid pump 18 (step u)), the closing of arterial patient tube clamp 5c, venous patient tube clamp 7c, possibly also of substituate clamp (infusate clamp), if not already accomplished (step v), and outputting an alarm or indication to inform the dialysis staff of the end of the process (step w). The step w) is in certain embodiments according to the present invention the final step of the method. In some embodiments according to the present invention, it is provided for the process to be already finished at one of the steps k) to u).

It should be noted that the sequence of steps, as set forth with reference to FIG. 2 is exemplary only. In fact, steps, though they are described successively, according to the present invention may also occur in other or reverse order, in so far as this is valid from the perspective of one skilled in the art. This is especially true for or particularly applies to the steps c), d) and e). The present invention also comprises other sequences and parallel course of the steps. The foregoing also applies to the steps i) and g). They can also be performed in parallel or in reverse order.

REFERENCE NUMBER LIST

| Reference number | Description |
| --- | --- |
| 1 | Blood treatment apparatus |
| 3 | Blood tube set |
| 4 | Dialysis fluid circuit |
| 5 | Arterial section |
| 5a | Arterial needle |
| 5c | Arterial patient tube clamp |
| 5d | Blood tube section |
| 6 | Dialysis fluid supply tube |
| 6c | Dialysis fluid supply tube clamp |
| 7 | Venous section |
| 7a | Venous needle |
| 7c | Venous patient tube clamp |
| 8 | Dialysate drain tube |
| 8c | Dialysate drain tube clamp |
| 9 | Blood filter |
| 11 | Membrane |
| 13 | Blood chamber |
| 15 | Dialysis fluid chamber |
| 17 | Blood pump |
| 18 | Dialysis fluid pump |
| 19 | Venous drip chamber |
| 19d | Vent valve |
| 19e | Sterile filter |
| 19f | Valve |
| 19g | Compressor |
| 19h | Pressure sensor |
| 21 | Control or regulating device |
| 35 | Patient |
| 37 | Air bubble detector |
| 39 | Venous blood sensor |

The invention claimed is:

1. A method for controlling a blood treatment apparatus, the blood treatment apparatus comprising (i) a blood pump for transporting blood in an extracorporeal blood tube set and (ii) a dialysis fluid pump for conveying dialysis fluid in a dialysis fluid circuit having a dialysis fluid supply tube which is adapted to be interrupted via a dialysis fluid supply tube clamp and a dialysis fluid drain tube which is adapted to be interrupted via a dialysis fluid drain tube clamp,
wherein the extracorporeal blood tube set (a) comprises an arterial section comprising or connected to at least one of an arterial needle or an arterial patient tube clamp, (b) comprises a venous section comprising or connected to at least one of a venous needle or a venous patient tube clamp, and (c) comprises or is connected to a blood filter arranged between the arterial section and the venous section, the blood filter comprising a membrane which separates a blood chamber from a dialysis fluid chamber, the method comprising:
(a) closing the arterial patient tube clamp and the venous patient tube clamp;
(b) conveying the dialysis fluid via the dialysis fluid pump;
(c) opening the venous patient tube clamp;
(d) closing the dialysis fluid drain tube;
(e) inhibiting or stopping a flow of the dialysis fluid, in particular, when a pre-defined or a predetermined first volume has passed through the membrane, wherein the pre-defined or the predetermined first volume is minus or less than a second volume, wherein the second volume corresponds to a volume of the arterial section up to an inlet of the blood filter;
(f) closing the venous patient tube clamp;
(g) conveying the dialysis fluid via the dialysis fluid pump;
(h) opening the arterial patient tube clamp while the dialysis fluid drain tube is closed;
(i) optionally reducing the flow rate via the dialysis fluid pump;
(j) closing the arterial patient tube clamp;
(k) stopping the dialysis fluid pump when the second volume has been delivered or air or clots have been detected via a sensor;
the method further comprising:
(A) (l) starting the dialysis fluid pump or an ultra-filtration pump located downstream of the blood filter;
(m) closing or holding or keeping closed the dialysis fluid supply tube;
(n) opening the dialysate fluid supply tube clamp;
(o) closing or holding or keeping closed the arterial and the venous patient tube clamps;
(p) opening a vent valve;
(q) sucking or aspirating dialysis fluid over the membrane and out of the extracorporeal blood tube set via the dialysis fluid pump;
(r) opening the dialysis fluid drain tube;
(s) introducing gas into a connecting line to a venous pressure sensor, which gas is configured to displace the dialysis fluid through the membrane into the dialysis fluid outlet side;
(t) optionally emptying a dry bicarbonate concentrate container;
(u) stopping the dialysis fluid pump;
(v) closing the arterial patient tube clamp and the venous patient tube clamp if the clamps are open; and
(w) outputting an alarm or indication that the method is finished; or
(B) (l) starting the dialysis fluid pump or an ultra-filtration pump located downstream of the blood filter;
(m) closing or holding or keeping closed the dialysis fluid supply tube;
(n) opening the dialysis fluid supply tube clamp;
(o) closing or holding or keeping closed the arterial and the venous patient tube clamps;
(p) opening a vent valve; and
(q) sucking or aspirating dialysis fluid over the membrane and out of the extracorporeal blood tube set via the dialysis fluid pump; or
(C) (r) opening the dialysis fluid drain tube; and
(s) introducing gas into a connecting line to a venous pressure sensor, which gas is configured to displace the dialysis fluid through the membrane into the dialysis fluid outlet side.

2. The method according to claim 1, further comprising: stopping the blood pump if a predetermined timing, duration of treatment, value of dialysis dose, or amount of ultra-filtration is reached.

3. The method according to claim 1, further comprising: ejecting a blood tube section of the extracorporeal blood tube set.

4. The method according to claim 1, wherein the dialysis fluid rate is automatically adjusted in step (b).

5. The method according to claim 1, further comprising at least one of:
separating at least one of a dialysate connector or an on-line connector or inhibiting, via at least one valve, a fluid communication between the connectors and hydraulics; or
disconnecting the container with dry bicarbonate concentrate from the hydraulics or preventing fluid communication between the container and the hydraulics.

6. The method according to claim 5, wherein disinfection is continued and terminated after detecting that the dialysate tubes have been connected to the machine, the online connector is in the rinsing position and the container of dry bicarbonate concentrate has been removed.

7. The method according to claim 1, further comprising:
    calculating the pre-defined or the predetermined first volume to the ultra-filtration amount.

\* \* \* \* \*